(12) United States Patent
Zada (10) Patent No.: US 11,684,634 B2
(45) Date of Patent: Jun. 27, 2023

(54) SODIUM PERCARBONATE DISSOLVING BATH PRODUCT FORMULATION

(71) Applicant: SOAKNESS LLC, Los Angeles, CA (US)

(72) Inventor: Gabriel Zada, Los Angeles, CA (US)

(73) Assignee: SOAKNESS LLC, Los Angeles, CA (US)

( * ) Notice: Subject to any disclaimer, the term of this patent is extended or adjusted under 35 U.S.C. 154(b) by 0 days.

(21) Appl. No.: 17/595,640

(22) PCT Filed: Mar. 9, 2021

(86) PCT No.: PCT/US2021/021558
§ 371 (c)(1),
(2) Date: Nov. 19, 2021

(87) PCT Pub. No.: WO2021/183551
PCT Pub. Date: Sep. 16, 2021

(65) Prior Publication Data
US 2022/0409656 A1    Dec. 29, 2022

Related U.S. Application Data

(60) Provisional application No. 62/987,709, filed on Mar. 10, 2020.

(51) Int. Cl.
*A61K 33/00* (2006.01)
*A61K 33/06* (2006.01)
(Continued)

(52) U.S. Cl.
CPC .............. *A61K 33/00* (2013.01); *A61K 33/06* (2013.01); *A61K 33/40* (2013.01); *A61K 36/899* (2013.01)

(58) Field of Classification Search
None
See application file for complete search history.

(56) References Cited

U.S. PATENT DOCUMENTS 4,812,308 A * 3/1989 Winston ............... A61K 8/22
424/53
4,853,266 A * 8/1989 Cullen ............... B65D 81/264
206/204

(Continued)

FOREIGN PATENT DOCUMENTS

WO   WO 2002/102948     12/2002
WO   WO 2007/099398      9/2007
WO   WO-2009004294 A1 *  1/2009 .......... C11D 17/046

OTHER PUBLICATIONS

International Search Report for Application No. PCT/US21/21558, dated May 18, 2021, 3 pages.

(Continued)

*Primary Examiner* — Ernst V Arnold
(74) *Attorney, Agent, or Firm* — Knobbe, Martens, Olson & Bear, LLP (57) ABSTRACT

Disclosed herein are embodiments of therapeutic substances that contain solid sodium percarbonate for use in a bath, and packaging for the therapeutic substances. The solid sodium percarbonate can be dissolved in a liquid, such as water, to produce a hydrogen peroxide solution. Hydrogen peroxide solutions can be provide beneficial effects to a user. The titrated sodium percarbonate can be mixed with other chemicals/materials in a pre-made packaging for ease of storage and using with a bath.

20 Claims, 4 Drawing Sheets

(51) Int. Cl.
*A61K 33/40* (2006.01)
*A61K 36/899* (2006.01)

(56) References Cited

U.S. PATENT DOCUMENTS

| | | | |
|---|---|---|---|
| 5,398,850 A * | 3/1995 | Sancoff | B01J 7/02 |
| | | | 222/399 |
| 9,334,468 B2 * | 5/2016 | Sunder | C11D 3/505 |
| 9,863,131 B2 | 1/2018 | Irwin et al. | |
| 2009/0176683 A1 | 7/2009 | Choe et al. | |
| 2010/0034889 A1 | 2/2010 | Rau et al. | |
| 2010/0209021 A1 | 8/2010 | Blythe et al. | |
| 2012/0067764 A1 | 3/2012 | Wiedemann et al. | |

OTHER PUBLICATIONS

Written Opinion for Application No. PCT/US21/21558, dated May 18, 2021, 8 pages.

* cited by examiner

SODIUM PERCARBONATE DISSOLVING BATH PRODUCT FORMULATION

PRIORITY CLAIM AND INCORPORATION BY REFERENCE

The present application is a 35 U.S.C. 371 of International Application No. PCT/US2021/021558, filed on Mar. 9, 2021, titled SODIUM PERCARBONATE DISSOLVING BATH PRODUCT FORMULATION, which claims the benefit of U.S. Provisional Application No. 62/987,709, filed Mar. 10, 2020, and titled SODIUM PERCARBONATE DISSOLVING BATH PRODUCT FORMULATION, the contents of this priority application is hereby incorporated by reference herein in its entirety as if fully set forth herein. The benefit of priority is claimed under the appropriate legal basis including, without limitation, under 35 U.S.C. § 119 (e). Any and all applications for which a foreign or domestic priority claim is identified in the Application Data Sheet as filed with the present application are hereby incorporated by reference herein in their entirety and made a part of this specification.

FIELD OF THE DISCLOSURE

Embodiments of the disclosure generally relate to dissolvable therapeutic substances for use in water, such as in a bath.

BACKGROUND

Dissolvable bath products such as bath salts are popular products. Dissolvable bath products may include ingredients that may be added to bath water to alter the bath water to make bath water more enjoyable. While bath products are typically recreational such as add fragrance to the bath water, bath products may also have therapeutic effects that can be beneficial for a user.

SUMMARY OF SOME EXEMPLIFYING EMBODIMENTS

Disclosed herein are embodiments of a therapeutic substance for human or animal use comprising solid sodium percarbonate. Also disclosed herein are embodiments of a therapeutic substance comprising sodium percarbonate. Further disclosed herein are embodiments of a method of adding sodium percarbonate to a bath or sink in order to produce hydrogen peroxide, and stabilizing the product for general use, storage, or shipping.

Additionally, disclosed herein are embodiments of a composition of matter comprising sodium percarbonate, in addition to a combination of any of the following: sodium bicarbonate, surfactant, citric acid, fragrance (e.g., Eucalyptus, lavender, menthol, vetiver), bentonite (clay), colloidal oatmeal, magnesium sulfate (Epsom salt), and additional bath salts (e.g. dead sea salts).

Disclosed herein are embodiments of a single-use or quantized, multi-use package or container containing the therapeutic substance. Also disclosed herein are embodiments of therapeutic substances that contain solid sodium percarbonate for use in a bath, and packaging for the therapeutic substances. The solid sodium percarbonate can be dissolved in a liquid, such as water, to produce a hydrogen peroxide solution. Hydrogen peroxide solutions can be provide beneficial effects to a user. The titrated sodium percarbonate can be mixed with other chemicals/materials in a pre-made packaging for ease of storage and using with a bath.

Disclosed herein are embodiments of a packet or packets of a therapeutic substance that can each include sodium percarbonate, sodium bicarbonate, clay, and/or magnesium sulfate. The packet can have a pressure relief valve coupled with the packet. The valve can be configured to allow a passage of a gas (that may build up within the packet during storage) within the packet to pass through the valve when a pressure level within the packet reaches or exceeds a predetermined value and to prevent or inhibit a passage of a gas or vapor from outside of the packet to flow through the valve into the packet.

Any embodiments of the therapeutic substances, the packets of therapeutic substances, or the methods of creating a therapeutic solution disclosed herein can include, in additional embodiments, one or more of the following features, components, and/or details, in any combination with any of the other features, components, and/or details of any other embodiments disclosed herein: wherein the therapeutic substance creates a therapeutic solution that can include hydrogen peroxide when the therapeutic substance is added to water; wherein the therapeutic substance is specifically designed for quantized usage in a bath, for enhanced shelf life, and/or for improved storage and transport; wherein the therapeutic substance can further include a surfactant; wherein the therapeutic substance can further include a fragrance; wherein the packet contains only approximately 4 oz of the therapeutic substance; wherein the therapeutic substance contains solid sodium percarbonate at a total weight percentage of between 10% and 15%; wherein the sodium percarbonate is a solid sodium percarbonate that is dissolvable in water; and/or wherein, when the solid sodium percarbonate is dissolved in water, a solution of hydrogen peroxide is created; wherein the total amount of the therapeutic substance in the packet is in a quantity that is configured for a single use within a bathtub.

Disclosed herein are methods of creating a therapeutic solution in a bathtub, wherein the method can include providing a packet including a therapeutic substance including a solid sodium percarbonate, filling the bathtub with water, and adding the contents of the packet to the water in the bathtub. Any embodiments of the therapeutic substances, the packets of therapeutic substances, or the methods of creating a therapeutic solution disclosed herein can include, in additional embodiments, one or more of the following features, components, and/or details, in any combination with any of the other features, components, and/or details of any other embodiments disclosed herein: wherein the packet contains approximately 4 oz of the therapeutic substance containing solid sodium percarbonate at a total weight percentage of between 10% and 15%; wherein, after adding the therapeutic substance from the packet to the water in the bathtub, the solid sodium percarbonate dissolves in the water and forms a solution of hydrogen peroxide with the water; and/or wherein the water is at a temperature above room temperature.

Disclosed herein are embodiments of a therapeutic substance, that can include any combination of sodium percarbonate, sodium bicarbonate, fragrance, clay, colloidal oatmeal, magnesium sulfate, and silicon dioxide. Any embodiments of the therapeutic substances, the packets of therapeutic substances, or the methods of creating a therapeutic solution disclosed herein can include, in additional embodiments, one or more of the following features, components, and/or details, in any combination with any of the other features, components, and/or details of any other embodiments disclosed herein: wherein the sodium percarbonate can have at a total weight percentage of between 10% and 15% of the therapeutic substance; wherein the fragrance comprises Eucalyptus, lavender, menthol, and/or vetiver; wherein the Eucalyptus comprises Eucalyptus *globulus* leaf oil; wherein the clay comprises bentonite; wherein the bath salt comprises dead sea salts; wherein the silicon dioxide comprises silica; wherein the therapeutic substance further includes a surfactant.

DETAILED DESCRIPTION OF SOME EXEMPLIFYING EMBODIMENTS

Disclosed herein are embodiments of a therapeutic substance 100 (also referred to herein as formulations or therapeutic formulations)) and packaging 102 therefore that can be used to form a therapeutic solution 108. Some embodiments of the therapeutic substance 100 and/or the therapeutic solution 108 can be used for soaking all or a portion of a human or animal body, such as in a bath tub, or for soaking a portion of the body such as a user's feet, hands, fingers, etc., though the therapeutic substance 100 can have other applications as well. In any embodiments, the therapeutic substance 100 and/or the therapeutic solution 108 can be for human or animal use.

Some embodiments of the therapeutic substance 100 can include sodium percarbonate (SPC), which has the chemical formula $Na_2H_3CO_6$, such as solid sodium percarbonate. When solid sodium percarbonate mixes with a liquid 106 such as water, it may dissolve into hydrogen peroxide which has a chemical formula $H_2O_2$ to form a therapeutic solution 108 having hydrogen peroxide. The liquid 106 may at least partially contain water. In some embodiments, the liquid 106 may be heated in order to allow the sodium percarbonate to more readily dissolve. However, in other embodiments, the liquid 106 may be room temperature or cooler. In some embodiments, the therapeutic substance 100 can include sodium percarbonate intermixed with one or more other chemicals, substances, or materials, though in some embodiments, the therapeutic substance 100 can be pure or approximately pure sodium percarbonate. Any embodiments disclosed herein can include any of sodium carbonate peroxyhdrate, sodium bicarbonate, sodium carbonate, and sodium bicarbonate, or any combination of any of the foregoing, in combination with any of the other substances or chemicals disclosed herein.

Figures 3A, 3B:
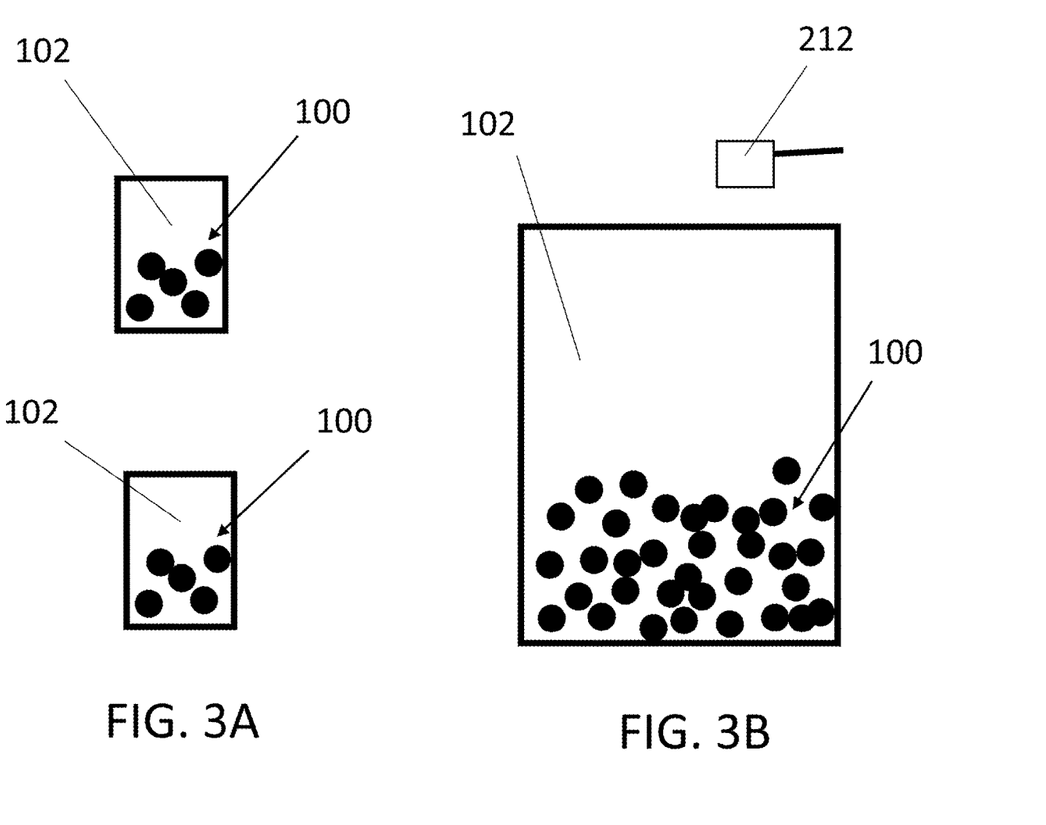
FIG. 3A illustrates an embodiment of a bath product packaged within single-use products.
FIG. 3B illustrates an embodiment of a bath product packaged within a multi-use product.

Some embodiments of the therapeutic substance 100 can be, for example and without limitation, packaged in one or more single use package 104, as shown in FIG. 3A, that can be pre-titrated to the size of a standard bathtub, opened and poured into a bath or bath sized container according to a pre-titrated or pre-specified amount that is designed for a single bath use. However, the particular packaging is not so limited. In other embodiments, the therapeutic substance 100 can be packaged in any desired size package, for example, a multi-use package, smaller packages for smaller containers, such as for soaking a user's feet or other appendages, for example and without limitation. In other embodiments, multi-use resealable packaging may be used and contain a quantized amount of the therapeutic substance 100 to be used in a predetermined number of bath treatments or bathtubs, for example 5 bath treatments, or from 4 to 10 bath treatments, or from 6 to 8 bath treatments. The individual, quantized amounts can be contained in separate pouches, bags, or other containers within the multi-use package.

As discussed above, the sodium percarbonate can be configured to dissolve in a body of water such as bath or sink water to form a therapeutic solution 108 having hydrogen peroxide. Hydrogen peroxide can have medical and health-related benefits. For example, hydrogen peroxide can have disinfectant and antiseptic properties, and can be used topically on the skin to prevent any infection caused by minor cuts, bruises or burns. In addition, hydrogen peroxide may provide oxygenation, pH balancing, and detoxification of skin. Hydrogen peroxide may also cleanse dead skin cells.

Soaking a user's body or portion of a user's body in a therapeutic solution 108 having hydrogen peroxide, such as from some embodiments of the therapeutic substance 100 disclosed herein, offers multiple benefits including skin oxygenation, helping fight infections, helping balance skin pH, and skin detoxification. Embodiments of the therapeutic solution 108 having hydrogen peroxide disclosed herein can help alleviate common symptoms associated with cold, flu, skin disorders, infections, and a variety of other conditions. Hydrogen peroxide baths may also help alleviate side effects of treatments (e.g., the side effects from cancer treatments such as chemotherapy).

Accordingly, disclosed herein is an all-in-one therapeutic substance 100 designed specifically for convenience in a standard bathtub with regard to packaging and storage, that can be used in a bath in which the formulation contains the ingredient sodium percarbonate, a chemical substance that is a solid at room temperature and releases hydrogen peroxide when mixed with water. Specifically, when dissolved in water, the sodium percarbonate of some embodiments disclosed herein yields a mixture of hydrogen peroxide (which eventually decomposes into water and oxygen), sodium cations (Na+), and carbonate.

Figure 1:
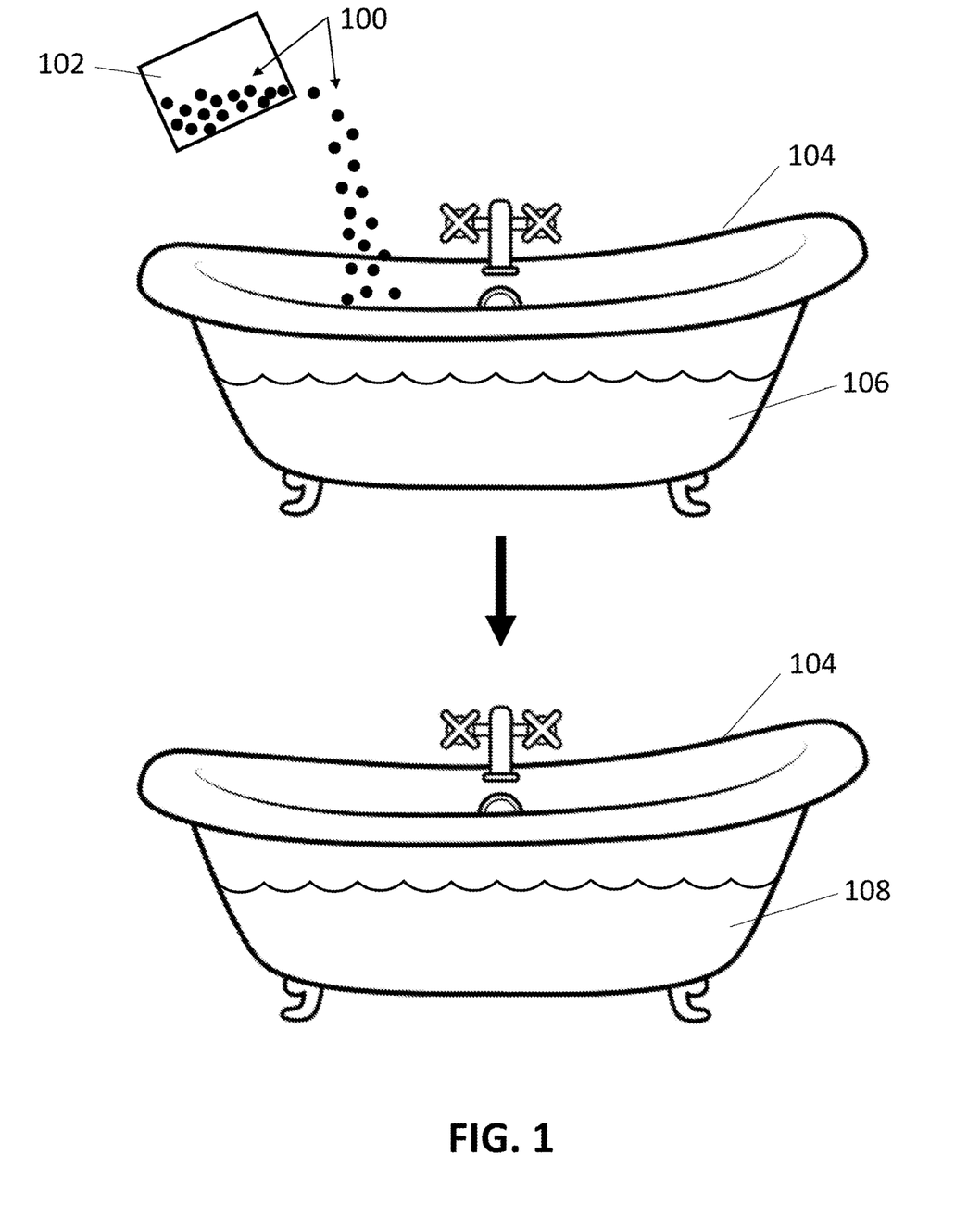
FIG. 1 illustrates a side view of an example of a bath product being added to liquid within a container.

FIG. 1 illustrates a side view of an embodiment of the therapeutic substance 100 being added to liquid (which can be, for example and without limitation, water) in a bathtub 104. In any embodiments disclosed herein, the therapeutic substance 100 can be added to a liquid in any desired type of container. A packet 102 containing the therapeutic substance 100 is illustrated. Some embodiments of the packet 102 can be a multi-use packet including more bath product 100 than needed or recommended for a single use, and/or a predetermined amount to use in a certain number of baths. Some embodiments of the packet 102 can be single-use packets which include only enough bath product 100 for one use. As illustrated, the therapeutic substance 100 can be poured out of the packet 102 and into a container 104 (such as a bathtub) filled with liquid 106. The therapeutic substance 100 includes a dissolvable solid that can include sodium percarbonate and other compounds and substances. The liquid 106 may be water or a liquid that contains at least some water. The container 104 may be a bath, sink, basin, tub, bucket, or bathtub capable of soaking at least a portion of a user's body. Some embodiments of the single use packet 102 can be configured for use with 25 gallons of liquid 106, or approximately 25 gallons of liquid 106 within the container 104, though not limited to these quantities. Some embodiments of the single use packet 102 can be configured for use with from 10 gallons (or approximately 10 gallons, or less than 10 gallons) of liquid 106 to 50 gallons (or approximately 50 gallons, or more than 50 gallons) of liquid 106, or for use with from 15 gallons (or approximately 15 gallons) of liquid 106 to 45 gallons (or approximately 45 gallons) of liquid 106, or for use with from 20 gallons (or approximately 20 gallons) of liquid 106 to 40 gallons (or approximately 40 gallons) of liquid 106, or for use with from 20 gallons (or approximately 20 gallons) of liquid 106 to 35 gallons (or approximately 35 gallons) of liquid 106, or for use with from 20 gallons (or approximately 20 gallons) of liquid 106 to 30 gallons (or approximately 30 gallons) of liquid 106.

Assuming a standard, average bathtub size of 25 gallons, embodiments of the therapeutic substance 100 disclosed herein can be a single-use or multi-use packet 102 containing of a mixture of ingredients in dissolvable solid (salt) form that could be added to a warm water tub as a topical (non-ingested) agent. In other embodiments, the therapeutic substance 100 can be in a fully liquid solution form or include non-salt based solids. For example, in some embodiments, the solid sodium percarbonate can be pre-dissolved to form a high strength liquid and then added to the bathtub. Also, the solid sodium percarbonate can be in another crystallographic form that would not qualify as a salt but is in a solid form. Further, any embodiments of the therapeutic substance 100 can be added to sinks, showers, smaller containers, and otherwise. After adding the therapeutic substance 100 including sodium percarbonate to the liquid 106, the sodium percarbonate can dissolve into the liquid 106, thereby making a solution 106a of hydrogen peroxide.

In some embodiments, without limitation, the standard packet size could, for example, contain 2 to 10 oz. (or approximately 2 to approximately 10 oz.) or, in some embodiments, 4 oz. (or approximately 4 oz.), of solid substance. In some embodiments, the packet 102 can include from 2 (or approximately 2) oz. to 8 (or approximately 8) oz., or from 3 (or approximately 3) oz. to 7 (or approximately 7) oz., or from 3.5 (or approximately 3.5) oz. to 6 oz. (or approximately 6) oz., or from 3.5 (or approximately 3.5) oz. to 5 (or approximately 5) oz. In some embodiments, adding 4 oz. of solid sodium percarbonate to a 25 gallon bathtub would be the equivalent of pouring 64 ounces of 3% hydrogen peroxide solution into a 25 gallon bathtub. However, other sizes/weights can be used as well, and the particular size/weight is not limiting. In some embodiments, one single use packet 102 can be configured to produce hydrogen peroxide in a 25 gallon bathtub that would be the equivalent of adding from 32 oz. (or approximately 32 oz.) to 96 oz. (or approximately 96 oz.), 40 oz. (or approximately 40 oz.) to 90 oz. (or approximately 90 oz.), 45 oz. (or approximately 45 oz.) to 85 oz. (or approximately 85 oz.), or 55 oz. (or approximately 55 oz.) to 75 oz. (or approximately 75 oz.) of 3% hydrogen peroxide solution into a 25 gallon bathtub. In some embodiments, a resealable bag would contain 16 oz. of product and be titrated to and used for 4 separate baths (4 oz each).

Thus, disclosed herein are embodiments of a novel chemical formulation and compound which can be used as a bath product, a design for its stabilization and storage, as well as a bath product including the chemical compound. Some embodiments of the therapeutic substance 100 can include a pre-titrated or pre-dosed amount of sodium percarbonate offered in a single use or multi use formulation, along with other substances as desired, such as fragrances, etc.

Figure 2:
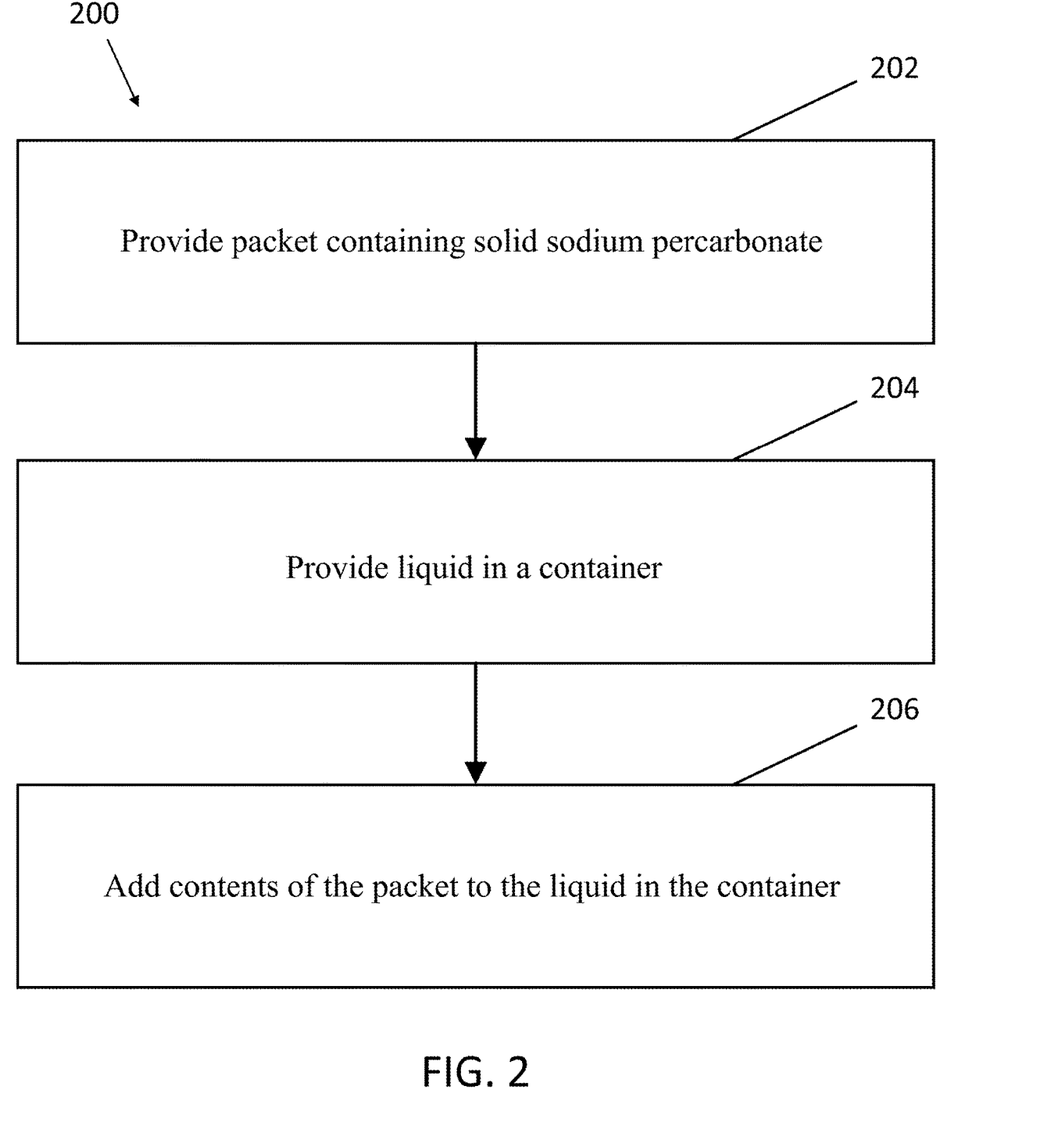
FIG. 2 illustrates an example method of dissolving solid sodium percarbonate to create hydrogen peroxide.

FIG. 2 illustrates a method 200 of dissolving solid sodium percarbonate to create hydrogen peroxide. At step 202, a packet containing solid sodium percarbonate is provided. The packet may be sized and configured for a single use or for multiple uses. The packet may contain other ingredients such as sodium bicarbonate or surfactant. Step 204 includes providing a liquid 106 in a container 104. The liquid 104 may be water or a solution containing water. The water may be bath water or sink water. The container 106 may be a sink, bath, bathtub, basin, bucket, or any vessel capable of holding the liquid while a user soaks at least a portion of their body. The liquid may be at room temperature or may be heated above room temperature which may aid in dissolving the solid sodium percarbonate. At step 206, the contents of the packet are added to the liquid 106 in the container 104. When the packet 102 is single use, the entire contents of the packet 102 can be added to the liquid 106 in the container 104. When the packet 102 is multi-use packet, the user can add only a portion of the contents of the package 102 to the liquid 106 in the container 104. The contents of the packet 102 dissolve in the liquid 106 in the container 104 to form a therapeutic solution 108 having hydrogen peroxide and other beneficial substances.

In some embodiments, the therapeutic substance 100 can include any or all of the following chemicals or substances, or any combination and/or amount of the following chemicals or substances:

Sodium percarbonate
Sodium bicarbonate
Clay (e.g. bentonite)
Colloidal oatmeal
Magnesium Sulfate (Epsom Salt)
Silicon dioxide In some embodiments, the therapeutic substance 100 can include any or all of the following chemicals or substances, or any combination and/or amount of the following chemicals or substances:

Sodium percarbonate
Sodium bicarbonate
Fragrance (e.g., Eucalyptus, lavender, menthol, and/or vetiver)
Clay (e.g. bentonite)
Colloidal oatmeal
Magnesium Sulfate (Epsom Salt)
Silicon dioxide In any embodiments disclosed herein, for example and without limitation, the therapeutic substance 100 can include 12.5% (or approximately 12.5%) SPC, or from 10% (or approximately 10%, or less than 10%) to 40% (or approximately 40%, or more than 40%) SPC, or from 10% (or approximately 10%, or less than 10%) to 20% (or approximately 20%, or more than 20%) SPC, or from 10% (or approximately 10%, or less than 10%) to 15% (or approximately 15%) SPC, or 24.6 grams (or approximately 25 grams) of SPC per 4 oz. of therapeutic substance 100, or from 20 grams (or approximately 20 grams) to 30 grams (or approximately 30 grams) per 4 oz. of therapeutic substance 100, 2.5% (or approximately 2.5%) bentonite clay, or from 1% (or approximately 1%) to 5% (or approximately 5%) bentonite clay, and/or less than 1% (or less than approximately 1%) silicon dioxide.

However, certain ingredients can be removed or added depending on the desired final product. For example, the final product may further include citric acid or additional bath salts such as dead sea salts. The Eucalyptus may be in the form of Eucalyptus *globulus* leaf oil. The final product may also further include a surfactant.

FIG. 3A illustrates the therapeutic substance 100 packaged within multiple single-use packets 102, such as in individual packets or sachets. In some embodiments, each single use product packet 102 can include enough therapeutic substance 100 for one use or can include multiple singe use packets 102 which can be sized and configured for a single use or sized and configured for less than an amount designed for a single use such that two or more packets 102 can be used in a single tub or container 104 of liquid 106 so that a user can adjust or control a strength of the therapeutic solution 108.

FIG. 3B illustrates an embodiment of a packet 102 of the therapeutic substance 100, the packet 102 being sized and configured for multiple uses (two or more uses, or three or more uses, or 10 or more uses). A multi-use product packet 102 can be larger than a single use product packet 102 and thus can contain sufficient bath salt for multiple uses. Some embodiments of the multi-use product packet 102 can have a tub, a bucket, a pouch, a bag, or otherwise and can have a scooper 212 that can be used to scoop out the therapeutic substance 100. The scooper 212 can include measurements, gradations, or other markings that indicate the amount of therapeutic substance 100 that is in the scooper 212, and/or can include measurements, gradations, or other markings that indicate how much of the product 100 to use based on a volume of a liquid 106 that is in the tub or other container 104, that can be based on a predetermined or desired concentration of the therapeutic solution 108.

In some embodiments, the sodium percarbonate can be packaged separately or sequestered (e.g., in a two chamber aluminum packaging) from the other ingredients and would mix only upon being poured into the water solution. In some embodiments, the product could be formulated as a solid bath bomb or as a gel/plasma/colloidal form. Thus, other embodiments of the therapeutic substance 100 or the packet 102 for the therapeutic substance 100 are included herein.

The advantages of some embodiments of the therapeutic substance 100 disclosed herein are that users can have an all in one, pre-dosed peroxide bath product without the need to have liquid hydrogen peroxide available, or need to calculate/measure/titrate the amount of hydrogen peroxide needed based on its concentration and amount of water solvent. This convenient formulation and method of packaging and storage would allow users to carry the therapeutic substance 100 in a safe, single use packet and travel with the product, rather than having to carry liquids which may be volatile or unsafe to travel with. Additional benefits include the myriad potential health benefits associated with hydrogen peroxide, namely skin oxygenation, antisepsis, sterilization, wound healing, skin detoxification, skin pH balancing, and many others. Benefits may be realized for symptoms associated with conditions such as cold, flu, asthma, skin conditions, sexually transmitted diseases, yeast infections, and many others. Further, benefits may be realized for side effects of cancer treatments such as chemotherapy.

Figure 4:
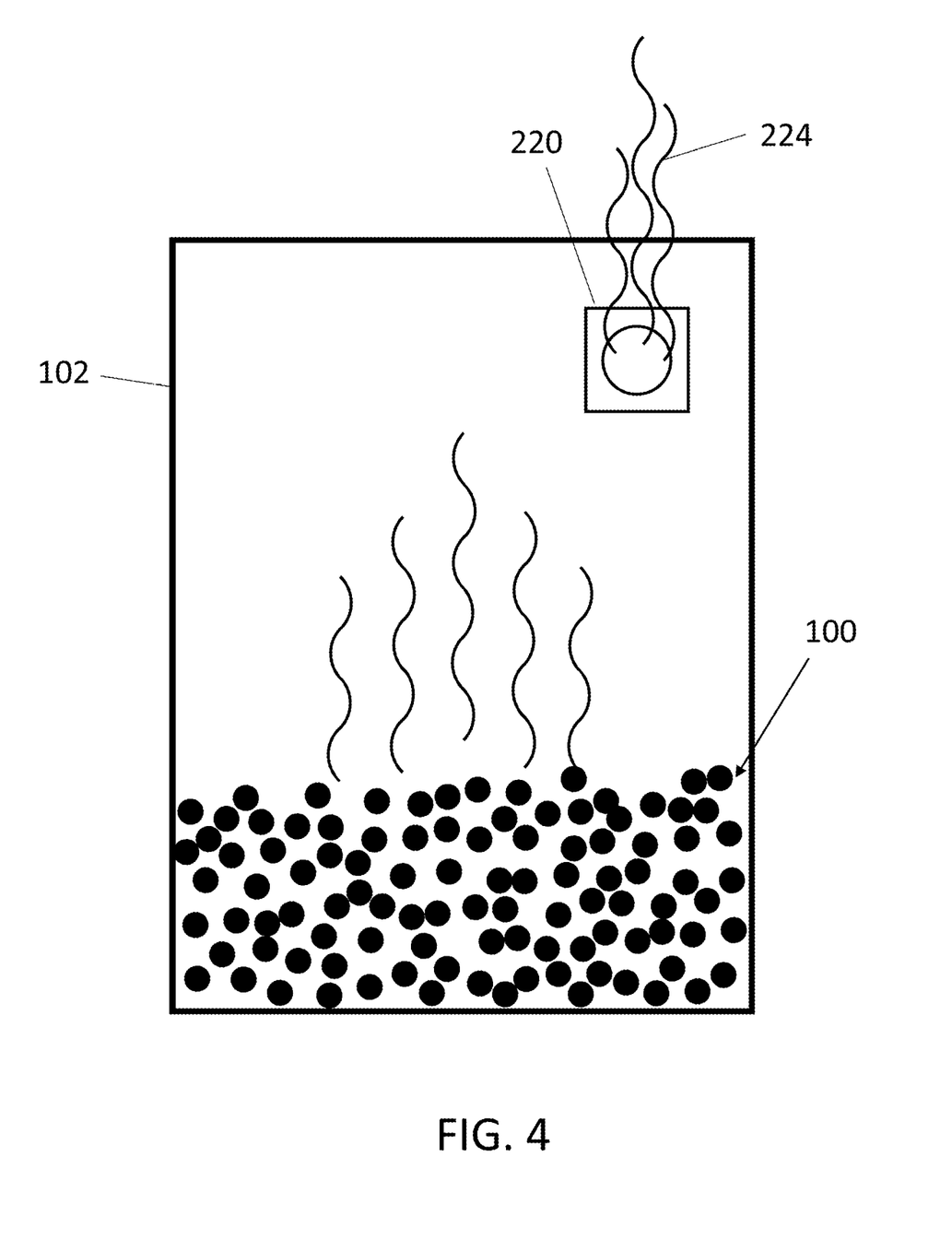
FIG. 4 illustrates an embodiment of a packet having an embodiment of a valve thereon.

In some embodiments, the therapeutic substance 100 can produce one or more gases (including $O_2$, $CO_2$, water vapor, and/or other gases) in the packet 102 that can cause a pressurization of the packet 102. In some embodiments, the gases can be caused by a degradation of or interaction of the chemicals or substances in the packet 102, or a reaction between a chemical or substance, or chemicals or substances, of the therapeutic substance 100 and air, moisture, or otherwise within the packet 102. To reduce a buildup of a positive pressure in the packet 102, some embodiments of the packet 102 can have a pressure relief valve 220 built into the packet 102, integrally formed with the packet 102, coupled with an opening in the packet 102, or otherwise used with the packet 102 to prevent a pressure within the packet 102 from exceeding a desired or threshold value. In some embodiments, the valve 220 can be a one-way valve, configured to permit a passage of a gas 224 from inside the packet 102 to pass through the valve 220 and into the ambient atmosphere while being configured to prevent any air, gas, liquid, or otherwise from passing from the ambient atmosphere through the valve 220 and into the packet 102. For example and without limitation, some embodiments of the valve 220 can be a one-way WICOVALVE™ or other diaphragm based valve, or have one or more components of a WICOVALVE. In some embodiments, the valve 220 can be configured to open when a pressure inside the packet 102 rises past a predetermined level. When the pressure within the packet 102 returns to a level that is near, approximately the same as, or less than the predetermined level, the valve 220 can close. Some embodiments of the valve 220 can be used to evacuate the gas or air within the packet 102, to create a vacuum within the packet 102.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A packet of a therapeutic substance, comprising:
   sodium percarbonate;
   sodium bicarbonate;
   clay; and
   magnesium sulfate; and
   a pressure relief valve coupled with the packet;
   wherein:
   the therapeutic substance is configured to create a therapeutic solution comprising hydrogen peroxide when the therapeutic substance is added to water;
   the valve is configured to allow a passage of a gas within the packet to pass through the valve when a pressure level within the packet reaches or exceeds a predetermined value and to prevent or inhibit a passage of a gas from outside of the packet to flow through the valve into the packet.

2. The packet of the therapeutic substance of claim 1, wherein the therapeutic substance is specifically designed for quantized usage in a bath, for enhanced shelf life, and/or for improved storage and transport.

3. The packet of the therapeutic substance of claim 1, further comprising a surfactant.

4. The packet of the therapeutic substance of claim 1, further comprising a fragrance.

5. The therapeutic substance of claim 4, wherein the fragrance comprises eucalyptus, lavender, menthol, and/or vetiver.

6. The packet of the therapeutic substance of claim 1, wherein the packet contains approximately 4 oz of the therapeutic substance.

7. The packet of the therapeutic substance of claim 1, wherein the therapeutic substance contains solid sodium percarbonate at a total weight percentage of between 10% and 15%.

8. The packet of the therapeutic substance of claim 1, wherein the sodium percarbonate is a solid sodium percarbonate that is dissolvable in water.

9. The packet of the therapeutic substance of claim 8, wherein, when the solid sodium percarbonate is dissolved in water, a solution of hydrogen peroxide is created.

10. The packet of the therapeutic substance of claim 1, wherein a total amount of the therapeutic substance in the packet is in a quantity that is configured for a single use within a bathtub.

11. The packet of the therapeutic substance of claim 1, wherein the sodium percarbonate has at a total weight percentage of between 10% and 15% of the therapeutic substance.

12. The packet of the therapeutic substance of claim 1, wherein the therapeutic substance further comprises colloidal oatmeal.

13. A method of creating a therapeutic solution in a bathtub, the method comprising:
    filling the bathtub with water; and
    adding the contents of the packet of claim 1 to the water in the bathtub;

wherein the therapeutic substance comprises solid sodium percarbonate at a total weight percentage of between 10% and 15%.

14. The method of claim 13, wherein, after adding the therapeutic substance from the packet to the water in the bathtub, the solid sodium percarbonate dissolves in the water and forms a solution of hydrogen peroxide with the water.

15. The method of claim 13, wherein the water is at a temperature above room temperature.

16. The method of claim 13, wherein the therapeutic substance further comprises colloidal oatmeal.

17. The method of claim 13, wherein the therapeutic substance further comprises dead sea salts.

18. The method of claim 13, wherein the therapeutic substance further comprises a fragrance.

19. The packet of the therapeutic substance of claim 1, wherein the therapeutic substance is a powder.

20. The method of claim 13, wherein the packet comprises approximately 4 oz of the therapeutic substance.

\* \* \* \* \*

UNITED STATES PATENT AND TRADEMARK OFFICE
CERTIFICATE OF CORRECTION

PATENT NO. : 11,684,634 B2
APPLICATION NO. : 17/595640
DATED : June 27, 2023
INVENTOR(S) : Gabriel Zada It is certified that error appears in the above-identified patent and that said Letters Patent is hereby corrected as shown below:

In the Specification

In Column 3, Line 57, delete "peroxyhdrate," and insert -- peroxyhydrate, --.

In Column 8, Lines 64-65, delete "sub combination." and insert -- subcombination. --.

In the Claims

In Column 10, Line 36, Claim 5, delete "The therapeutic" and insert -- The packet of the therapeutic --.

Signed and Sealed this
Twenty-fourth Day of October, 2023

Katherine Kelly Vidal
*Director of the United States Patent and Trademark Office*